United States Patent [19]
Pollak et al.

[11] Patent Number: 5,255,070
[45] Date of Patent: Oct. 19, 1993

[54] METHOD FOR DETERMINING INTERFACE PROPERTIES OF SEMICONDUCTOR MATERIALS BY PHOTOREFLECTANCE

[76] Inventors: Fred H. Pollak, 531 Main St., New York, N.Y. 10044; Hong-En Shen, 7 Country Club Rd., Apt. 29, Eatontown, N.J. 07724; Gerald Lucovsky, 124 Lockwood West, Cary, N.C. 27511

[21] Appl. No.: 382,190

[22] Filed: Jul. 20, 1989

[51] Int. Cl.[5] ............................................. G01N 21/25
[52] U.S. Cl. ..................................... 356/417; 356/432
[58] Field of Search .................... 356/432 T, 319, 445, 356/432, 417

[56] References Cited

U.S. PATENT DOCUMENTS

| | | | |
|---|---|---|---|
| 4,142,802 | 3/1979 | Pollak et al. | 356/319 |
| 4,807,991 | 2/1989 | Carew | 356/72 |
| 4,889,565 | 12/1989 | Fan et al. | 136/256 |

OTHER PUBLICATIONS

Shen et al, "New Normalization Procedure for Modulation Spectroscopy," Rev. Sci. Instrum. vol. 58, #8, Aug. 1987, pp. 1429–1432.

Glembocki et al, "Photoreflectance Characteristics of GaAs/AlGaAs Thin Films, Heterojunctions and Multiple Quantum Well Structures," SPIE, vol. 524, Spectroscopic Characterization Techniques for Semiconductor Technology II, 1985 pp. 86–94.

Photoelectrochemistry and Electrosynthesis on Semiconductor Materials, Ginley et al, vol. 88-14, pp. 468–476.

Primary Examiner—Davis L. Willis
Assistant Examiner—K. P. Hantis
Attorney, Agent, or Firm—Paul M. Craig, Jr.

[57] ABSTRACT

A method for determining information about properties at interfaces of semi-conductor materials in which a probe bean monochromatic light is directed onto a material sample which is itself electromodulated by a modulated pump beam, whereby the light reflected from the sample is detected to produce a d.c. signal and an a.c. signal, and after normalizing the procedure, the shifts of energy gaps in the band gaps are evaluated to obtain information about at least one externally applied parameter crossing such shift.

4 Claims, 2 Drawing Sheets

METHOD FOR DETERMINING INTERFACE PROPERTIES OF SEMICONDUCTOR MATERIALS BY PHOTOREFLECTANCE

FIELD OF INVENTION

The present invention relates to a method for determining the characteristics of materials, particularly of semiconductors, semiconductor heterostructures and semiconductor interfaces by the use of photoreflectance and to an apparatus for carrying out the method.

BACKGROUND OF THE INVENTION

The importance to study and characterize semiconductors (bulk or thin film), semiconductor heterostructures (superlattices, quantum wells, heterojunctions) and semiconductor interfaces (Schottky barriers, metal-insulator-semiconductors, semiconductorelectrolyte, semiconductor-vacuum, etc.) assumes ever-greater significance, particularly as many of these semiconductors and semiconductor microstructures are fabricated by modern thin-film techniques such as molecular beam epitaxy (MBE), metal-organic chemical vapor deposition (MOCVD), etc.

The materials and interfaces grown by MBE and MOCVD as well as other methods can be characterized by a variety of optical, electronic and structural methods including photoluminescence, photoluminescence excitation spectroscopy, absorption spectroscopy, modulation spectroscopy, Raman and resonant Raman scattering, cyclotron resonance, Hall effect, transmission electron microscopy, etc. Each of these tools provides specific information about the material of interest. For characterization purposes the experimental tools should be as simple and informative as possible. Many of the methods mentioned above are specialized and sometimes difficult to employ. For example, a number thereof, such as photoluminescence, photoluminescence excitation spectroscopy, absorption, cyclotron resonance, generally require cryogenic temperatures. Because of its simplicity and proven utility, photoreflectance has recently gained importance for the evaluation of semiconductor thin films and heterostructures.

The basic idea of modulation spectroscopy is a very general principle of experimental physics. Instead of directly measuring an optical spectrum, the derivative with respect to some parameter is evaluated. This can easily be accomplished by modulating some parameter of the sample or measuring system in a periodic fashion and measuring the corresponding normalized change in the optical properties. The former perturbation is termed "external" modulation and includes such parameters as electric fields (electromodulation), temperature (thermomodulation), stress (piezomodulation), etc. Changes in the measuring system itself, e.g., the wavelength or polarization conditions can be modulated or the sample reflectance can be compared to a reference sample, are termed "internal" modulation.

In modulation spectroscopy uninteresting background structure is eliminated in favor of sharp lines corresponding to specific transitions between energy levels in the semiconductors and semiconductor microstructures. Also, weak features that may not have been seen in the absolute spectra are enhanced. While it is difficult to calculate a full reflectance (or transmittance) spectrum, it is possible to account for the lineshape of localized spectral features of modulation spectroscopy. The ability to fit the lineshape is an important advantage of modulation spectroscopy. Lineshape fits yield accurate values of the semiconductor energy gap as well as broadening parameter. In addition, since "external" modulation spectroscopy is the a.c. response of the system to the modulating parameter, photoreflectance also provides information in the other modulation variables such as phase, modulation frequency, modulation amplitude, modulation wavelength as will be discussed more fully hereinafter.

In photoreflectance, the built-in electric field of the materials is modulated by the photo-injection of electron-hole pairs created by a pump beam of wavelength $\lambda_p$ which is chopped at frequency $\Omega_m$. 1-13 Despite its utility, the mechanism of photoreflectance is not fully understood although several experiments have indicated that photoreflectance is due to the modulation of the built-in electric field through a recombination of the minority species with charge in traps. Thus, by measuring the dependence of the photoreflectance signal on $\Omega_m$ it is possible to gain information about trap tines with the use of photoreflectance.

Though the use of photoreflectance has been known for more than twenty years, experimental difficulties experienced with the photoreflectance method in relation to other modulation methods lessened interest in the photoreflectance. These difficulties included scattered light from the pump beam and photoluminescence from the sample. A report published in 1985 on the photoreflectance results on semiconductor heterostructures by Glembocki et al., Appl. Phys. Letts. 46, 970 (1985); *Proceedings of the SPIE* (SPIE, Bellingham, 1985) 524, 86 (1985) produced renewed interest in the use of photoreflectance to study not only these semiconductor structures but also to study bulk (thin film) material. An improved apparatus involving a new normalization procedure which was published in 1987, will be described hereinafter by reference to FIG. 1. The new normalization procedure involved in the apparatus of FIG. 1 helped to solve some of the aforementioned photoreflectance problems, i.e., scattered light from the pump beam and photoluminescence from the sample.

The present invention is concerned with further improving the prior art apparatus to achieve improved signal-to-noise ratios, to further eliminate problems encountered in the prior art apparatus and in particular to utilize novel computerized procedures to gain additional information on the characteristics of the materials examined.

Accordingly, it is an object of the present invention to provide an improved method and apparatus for determining the characteristics of certain materials by photoreflectance which avoid by simple means the shortcomings and drawbacks encountered with the prior art apparatus and methods in the use thereof.

Another object of the present invention resides in a novel apparatus which assures improved signal-to-noise ratio.

A further object of the present invention resides in an apparatus utilizing photoreflectance for determining characteristics of certain materials which is simple to use, provides great versatility in the information which can be obtained and assures high reliability and accuracy.

Still another object of the present invention resides in an apparatus utilizing conventional computer technologies to obtain information on additional characteristics of the materials.

Another object of the present invention resides in a method for determining characteristics of certain materials, such as semiconductor materials and semiconductor heterostructures, which is simple to use, reliable in its operation and accurate in the results obtained therewith.

Another object of the present invention resides in a method of utilizing photoreflectance which permits to obtain such additional information as temperature, uniformity of the sample tested and composition of the alloy.

Still another object of the present invention resides in a method based on photoreflectance which permits continuous monitoring in the manufacture of materials, such as semiconductor materials, that eliminates the shortcomings and drawbacks encountered with the prior art systems.

A further object of the present invention resides in a method based on photoreflectance which permits accurate quality control in the manufacture of semiconductor materials.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein.

DETAILED DESCRIPTION OF THE DRAWINGS

Figure 1:
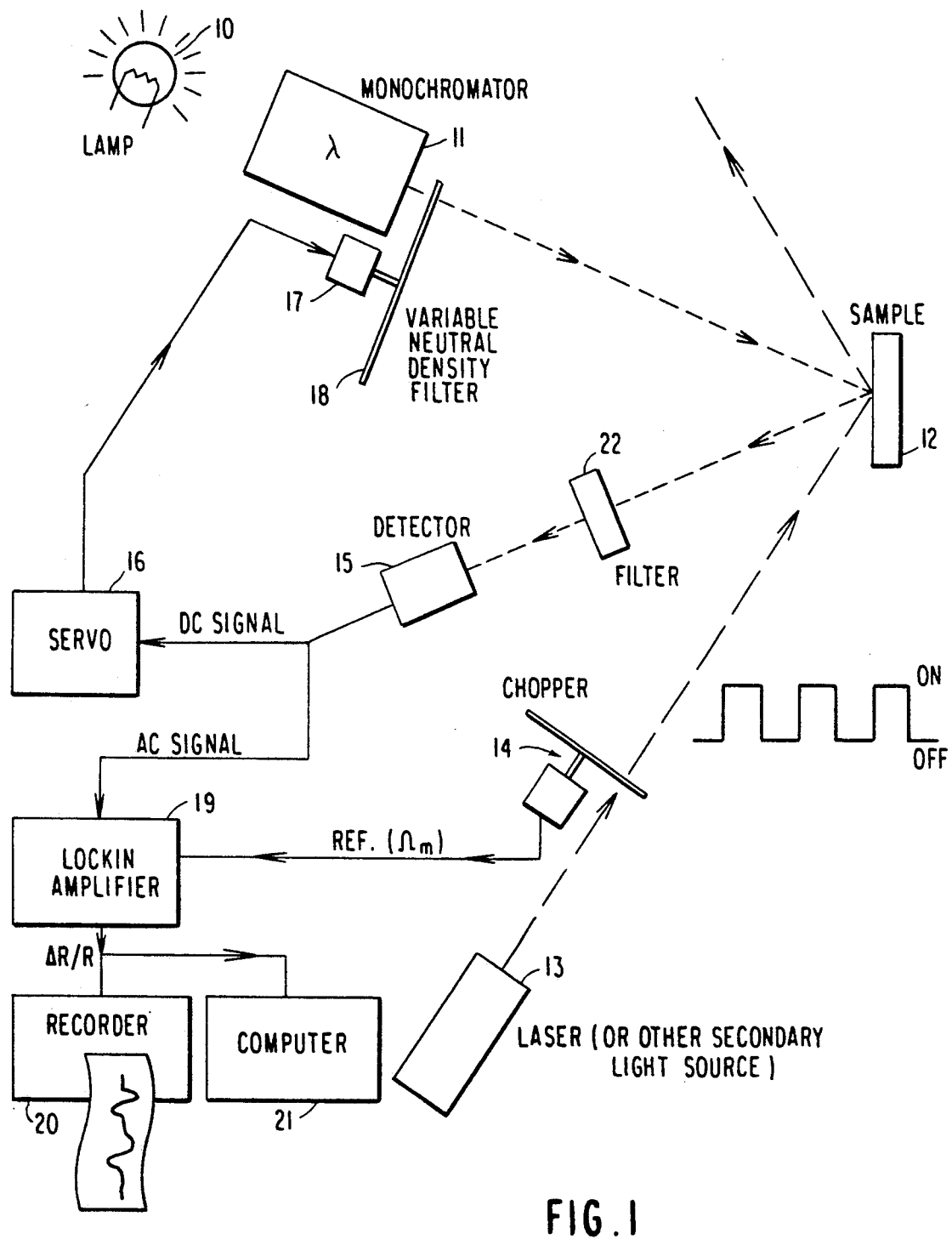
FIG. 1 is a schematic block diagram of a prior art apparatus utilizing photoreflectance.

Referring now to the drawing, and more particularly to FIG. 1, reference numeral 10 designates an appropriate lamp source whose light passes through a monochromator 11, to be referred to hereinafter also as probe monochromator. The exit intensity of the monochromator 11 at the wavelength $\lambda$ is focused onto a sample 12 by means of conventional lenses or mirrors (not shown). $I_o(\lambda)$ is thereby the intensity of light from the probe source 10, 11 striking the sample 12. Electromodulation of the sample 12 is produced by photoexcitation of electron-hole pairs created by a pump beam from a pump source 13. The pump beam can be a laser or a monochromator and is chopped by a conventional chopper 14 at a frequency $\Omega_m$. The beam reflected from the sample 12 is again collected by conventional second lenses or mirrors (not shown) and is focused on a detector 15, such as a photomultiplier, photodiode, photoconductor, etc. As the lenses or mirrors are of conventional construction, they are not shown for the sake of simplicity. Although FIG. 1 as well as FIG. 2 to be described more fully hereinafter show the configuration for reflectance, the experiment can also be readily modified for transmission by placing the detector behind the sample. Accordingly, the term photoreflectance (PR) is used in this application in a broad sense to encompass both reflectance and transmittance.

The output of the detector 15 contains two signals, i.e., the d.c. signal and the a.c. signal. The d.c. signal is applied to a servo unit 16 which drives a motor 17 controlling a variable neutral density filter 18 to achieve normalization as will be discussed more fully hereinafter. The a.c. signal from the detector is applied to a conventional lock-in amplifier 19 which also receives a reference signal $\Omega_m$ from the chopper 14. The desired signal $\Delta R/R$ contained in the output of the lock-in amplifier 19 is applied to a conventional recorder 20 for visual display of the information as well as to a computer 21 to permit line-shape fitting.

The light striking the detector 15 contains two signals: the d.c. (or average value) is given by $\alpha(\lambda)I_o(\lambda)R(\lambda)$ $[\alpha(\lambda)I_o(\lambda)T(\lambda)]$, where $\alpha(\lambda)$ is the optical response of the collecting lens (or mirror), $R(\lambda)[T(\lambda)]$ is the d.c. reflectance (transmittance) of the material while the modulated value at frequency $\Omega_m$ is $\alpha(\lambda)I_o(\lambda)\Delta R(\lambda)[\alpha(\lambda)\Delta T(\lambda)]$, where $\Delta R(\lambda)[\Delta T(\lambda)]$ is the modulated reflectance (transmittance). The a.c. signal from the detector 15, proportional to $\alpha I_o \Delta R(\alpha I_o \Delta T)$ is measured by the lockin amplifier 19. The a.c. and d.c. signals from the detector 15 are denoted as Vac and Vdc, respectively.

In order to evaluate the quantity of interest $\Delta R(\lambda)/R(\lambda)[\Delta T(\lambda)/T(\lambda)]$ a normalization procedure must be used to eliminate the uninteresting common feature $\alpha I_o$. In FIG. 1, normalization is achieved by the use of the variable neutral density filter 18 connected to the servo system 16, 17. The variable neutral density filter 18 is placed in the optical path between the probe monochromator 11 (or other probe source such as a dye laser) and the sample 12. The d.c. signal from the detector 15 ($V_{dc}$) is fed to the servo 16 which varies the variable neutral density filter 18 and hence $\alpha(\lambda)I_o(\lambda)$ in order to keep $V_{dc}$ as a constant. Thus, in this procedure, the operating conditions of the experiment, i.e., detector amplification, instrumental resolution, etc. are kept constant. In previous modulation experiments normalization was achieved by (a) either varying the operating conditions of the system such as amplification of the detector, entrance slit of the monochromator to control $I_o$ or (b) by electronically dividing $V_{ac}$ by $V_{dc}$.

As pointed out above in photoreflectance experiments, problems are caused by (a) diffuse reflected light from the pump source and (b) photoluminescence produced by the pump light getting into the detector 15. This latter problem is particularly acute at low temperatures (semiconductor and semiconductor structures) and for superlattices and quantum wells even at 77K and sometimes room temperature. A main goal in a photoreflectance measurement is therefore to eliminate diffuse reflected light from the modulation source and/or photoluminescence produced by the intense pump light. Both of them may reach the detector 15 and then produce a spurious signal in the lock-in amplifier 19. A filter 22 in front of the detector 15 in FIG. 1 assists in reducing the diffused light from the pump source.

The d.c. output of the photodetector 15, $V_{dc}$, can be written as:

$$V_{dc} = \alpha(\lambda)I_o(\lambda)R(\lambda)K(\lambda)A(\lambda) \qquad (1)$$

where $K(\lambda)$ is the detector response (including the response of a filter if it is used) and $A(\lambda)$ is the amplification factor of the detector.

In photoreflectance, the a.c. output ($V_{ac}$) is given by:

$$V_{ac} = [\alpha(\lambda)I_o(\lambda)R(\lambda)K(\lambda) + \alpha(\lambda_{sp})I_{sp}(\lambda_{sp})K(\lambda_{sp})]A(\lambda) \qquad (2)$$

where $I_{sp}$ is the intensity of the spurious signal due to scattering and/or photoreflectance and $\lambda_{sp}$ is the wavelength of the spurious signal. The second term in Equation (2) is generally missing from other forms of modulation spectroscopy such as electroreflectance, thermoreflectance, etc. (although it may occur in piezomodulation because of vibrations).

In the normalization procedure of FIG. 1, the quantity $V_{dc}$ is kept at some constant value C by varying $I_o(\lambda)$, the light intensity incident on the sample 12, by means of the variable neutral density filter 18. In such a procedure, the amplification of the detector 15 is not changed and hence $A(\lambda)=A$, where A is a constant. Thus, we can write $$\alpha(\lambda)I_o(\lambda)=C/R(\lambda)K(\lambda)A \qquad (3)$$

Substituting Equation (3) into Equation (2) yields for $S_{LIA}(=V_{ac}/V_{dc})$, the normalized output signal from the lock-in amplifier 19, the term:

$$S_{LIA}=[C\Delta R(\lambda)/R(\lambda)]+[\alpha(\lambda_{sp})I_{sp}(\lambda_{sp})K(\lambda_{sp})A] \qquad (4)$$

Since $\alpha(\lambda_{sp})$, $I_{sp}(\lambda_{sp})$, $K(\lambda_{sp})$ and A are all independent of the probe wavelength, the second term in Equation (4) is a constant. If this second term is not too large in relation to $C\Delta R/R$, it is fairly simple to subtract the spurious factor and recover the true signal $\Delta R/R$. It has been found that if $C\Delta R/R \geq 0.01(\alpha I_{sp}KA)$, the subtraction can be readily accomplished. The subtraction of the spurious signal is important for proper operation of the photoreflectance apparatus.

Figure 2:
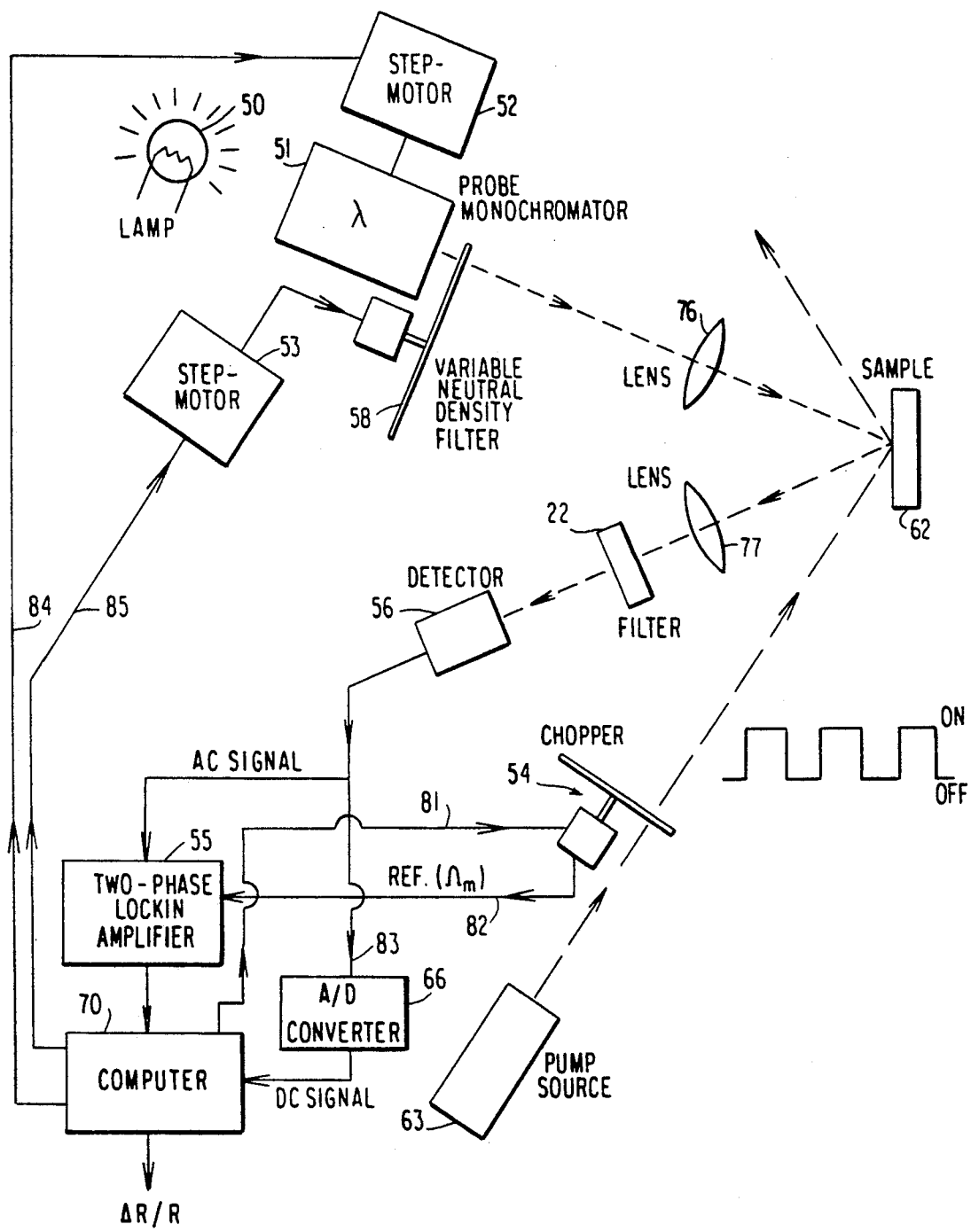
FIG. 2 is a schematic block diagram of an apparatus in accordance with the present invention which utilizes photoreflectance in combination with computer controls to increase accuracy and versatility of the equipment.

FIG. 2 is a schematic block diagram of a photoreflectance apparatus in accordance with the present invention. It differs from FIG. 1 in several important aspects. The probe monochromator 51 is driven by step-motor 52 which is controlled by the computer generally designated by reference numeral 70 of any conventional construction, programmed by conventional techniques to achieve the various functions, as will be described more fully hereinafter. Differing from FIG. 1, the variable neutral density filter 58 is not driven by a servo-mechanism but by a step-motor 53 which is also controlled by the computer 70. It has been found that the signal-to-noise ratio can be improved by a factor of 10 using the step-motor control of FIG. 2 instead of the servo system of FIG. 1. The improvement is probably attributable to the fact that the servo system involves small instabilities which are eliminated by the step-motor arrangement in accordance with the present invention in addition, the computer 70 also controls the frequency ($\Omega_m$) of the modulator 54, for instance, in the form of a conventional chopper modulating the pump beam emitted by the pump source 63. Furthermore, the lock-in amplifier 55 is a two-phase model of known construction which determines the in-phase and out-phase components of the photoreflectance signal (relative to the pump beam). The use of the two-phase lock-in amplifier 55 is important for evaluating the photoreflectance signal as a function of $\Omega_m$ to yield information about trap states as will be discussed more fully hereinafter. It has also been found that signals from different depth regions of a sample structure produce signals with different phases and dependence of $\Omega_m$ which can be sorted out by the two-phase lock-in amplifier 55 and the computer-controlled modulating frequency $\Omega_m$.

In the apparatus according to FIG. 2, the probe light produced by lamp 50 in conjunction with the probe monochromator 51, which can be adjusted by step-motor 52 to vary the wavelength $\lambda$ of the probe light, is directed onto sample 62 by the use of a lens(es) or mirror(s), schematically indicated by lens 76. The pump beam produced by the pump source 63 in the form of a laser or other appropriate secondary light source is also directed onto the sample 62 after being modulated by modulator 54 whose frequency $\Omega_m$ can be varied by computer 70 by way of line 81. The light reflected (transmitted) from the sample 62 is again directed onto detector 54 by a lens(es) or mirror(s), schematically indicated by lens 77. The detector 54 may be similar to detector 15 of FIG. 1 and a filter 22 may again be interposed in the optical path between the sample 62 and detector 54. The a.c. signal in the output of detector 54 is applied to the input of the two-phase lock-in amplifier 55 to which is also applied a reference signal ($\Omega_m$) from the modulator 54 by way of line 82 to provide information about the modulating frequency $\Omega_m$ for purposes which will be explained hereinafter. The d.c. signal from detector 54 is applied to computer 70 by way of line 83 which includes an A/D converter 66 to change the analog signal from detector 54 into a digital signal for use by the computer 70.

One output of computer 70 contains the desired photoreflectance signal $\Delta R/R$ which is applied to a user-friendly display, e.g the display screen (not shown) associated with the computer. Another output of computer 70 controls the step-motor 52 to vary the probe-light wavelength $\lambda$, by way of line 84. A further output of computer 70 controls the step-motor 53 to vary the adjustment of the variable neutral-density filter 58 by way of line 85, and still another output of computer 70 controls the frequency $\Omega_m$ of the modulator 54 by way of line 81, all for purposes to be explained more fully hereinafter.

COMPUTER FUNCTIONS

The computer 70 of any known type and with sufficient memories is programmed to provide the following functions. Since the programming involves conventional programming techniques, as known to persons skilled in the art, a detailed description thereof is dispensed with herein for the sake of simplicity.

The software used with computer 70 can be divided into three general functions which can be designated as (A) Control and Data Acquisition, (B) Data Analysis including lineshape fit of photoreflectance spectra and (C) Comparison of Relevant Parameters obtained from the Data Analysis with Theoretical Models.

A. Control/Data Acquisition Component

The control/data acquisition component serves the following functions:

(1) It controls the step-motor 53 which, in turn, varies the variable neutral density filter 58 in order to keep $V_{dc}$ as a constant for normalization purposes.

(2) It controls the step-motor 52 which drives the probe monochromator 51. Thus, the range of wavelength $\lambda$ for a given experiment can be set by the computer 70. Also, the computer 70 can control the step-motor 52 for multiple scans to accumulate a preset signal-to-noise ratio.

(3) The computer 70 records both the in-phase and out-phase components of the signal from the lock-in amplifier 55.

(4) The computer controls the chopping frequency $\Omega_m$. When measuring the dependence of the in-phase signal on $\Omega_m$, the computer 70 controls $\Omega_m$. In this case the amplification of the electronic system (detector, preamplifier, lock-in amplifier) may change with $\Omega_m$. The computer software automatically corrects for this.

(5) The computer control of a given experiment is an important function in the subtraction of the spurious signal $\alpha I_{sp}KA$ from the true photoreflectance signal $C(\Delta R/R)$. This is accomplished in the following manner. At a given probe beam wavelength ($\lambda$), which the computer 70 sets by means of step-motor 52, the computer sets the variable neutral density filter 58 for maximum density. Thus, the constant C (and $I_o$) in Equations (3) and (4) is made equal to zero. In this case $S_{LIA}(\lambda) = \alpha I_{sp}KA$. This signal is analyzed by the computer 70 to determine the absolute phase of the pump beam appearing at the input terminal of the lockin amplifier 55. Then the computer sets the lock-in amplifier 55 to the correct phase with respect to the optical pump and offsets the spurious signal by changing the zero setting of the lock-in amplifier 55. In the case of large spurious signals, this procedure is repeated at several different probe beam wavelengths.

B. Data Analysis/Fit

This component performs the following functions:

(1) It interfaces with components A and C.

(2) It presents the data (photoreflectance spectrum) on the computer screen in a user-friendly manner. For example, photon wavelength is converted to photon energy. Different spectral regions of the data can be presented in magnified form.

(3) It provides data transformation including Fast Fourier Transform, filtering and smoothing procedures to improve signal-to-noise ratio and derivatives and integrals to analyze signals.

(4) It provides lineshape fit to data to extract important parameters such as photon energy of spectral features, linewidth of spectral feature, amplitude and phase. This is an important aspect of the entire program.

(5) It fits to the dependence of the in-phase photoreflectance signal on chopping the frequency ($\Omega_m$). This fit can be used to obtain information about trap times.

(6) It provides vector analyses of the in-phase and out-phase components of a spectrum to distinguish signals from different depth regions of the sample.

(7) If Franz-Kaldysh oscillations are observed, it evaluates peak positions of the Franz-Kaldysh oscillations. This can be used to determine electric fields and sometimes carrier concentration.

C. Comparison of Relevant Parameters of Data with Theoretical Models

In software component B, various pieces of experexperimental information are obtained such as positions of energy gaps, peak positions of Franz-Kaldysh oscillations, etc. In order to make this data useful, it must be compared with various models to give the user information about the semiconductor or semiconductor structure.

(1) In thin film or bulk alloy raaterials, the position of the energy levels can be used to evaluate alloy composition. For example, in $Ga_{1-x}Al_xAs$ the Al composition (x) can be determined.

(2) In thin film or bulk elemental or binary semiconductors (GaAs, Si, etc.) the position of the energy gap can be used to determine the temperature of the material.

(3) From the evaluation of linewidth one can gain information about crystal quality.

(4) Strains can be determined from shifts and splittings of peaks.

(5) If Franz-Kaldysh oscillations are observed, positions of peaks can be used to evaluate the built-in electric field and in some cases carrier concentrations.

(6) From the dependence of the in-phase component on $\Omega_m$ and temperature T, one can evaluate activation energy of trap states.

(7) In semiconductor microstructures such as superlattices, quantum wells and multiple quantum wells a complex theoretical model can be compared to the experimentally determined energy gap to evaluate width of quantum wells and barriers, barrier height and in the case of lattice-mismatched systems (InGaAs), the built-in strain.

There is frequently a strong interaction between this aspect of the program and the lineshape fit discussed in software component B-4 above. In semiconductor microstructures the spectrum is often very complex and hence only major peaks will be fitted by the lineshape fit of software component B-4. This initial information is then fed into the theoretical model of software component C-7 to determine where other smaller features should be found. This information is then introduced into software component B-4 to complete the lineshape fit of the minor spectral features.

NEW APPLICATIONS

The present invention provides the following new applications of photoreflectance.

A. In-Situ Monitoring of Growth Conditions for MBE and MOCVD

It has recently been found that photoreflectance can be performed on GaAs and $Ga_{0.82}Al_{0.18}As$ at temperatures up to 600° C. These temperatures correspond to growth conditions for MBE and MOCVD. Thus by using photoreflectance the temperature of the GaAs substrate can be measured in a contactless manner to about ±10° C. to within a depth of only a few thousand Angstroms, i.e., near the growth surface. Also, in situ monitoring of the growth of epitaxial layers of $Ga_{1-x}Al_xAs$ can be performed. In both cases topographical scans can be performed to evaluate uniformity. The energy band gaps of semiconductors are functions of various parameters such as temperature, alloy composition (in the case of alloy semiconductors such as $Ga_{1-x}Al_xAs$), stress, etc. Thus by accurately measuring the position of the energy gap one can gain information about these quantities. For example, accurate determination of the band gap of GaAs can be used to determine its temperature. Thus, this application of photoreflectance makes use of the sharp, derivative-like structure and the lineshape fit to accurately determine the energy of the energy gap. At present the two main techniques to evaluate substrate temperatures over a wide range are infrared pyrometry and thermocouples in intimate contact with the back of a substrate holder. Both of these techniques have serious drawbacks. Thermocouples measure the temperature at the back of a relatively thick block of Mo to which the substrate is mounted by suitable means which may vary considerably in thickness and distribution from run to run. The actual surface temperature of the substrate is thus known to within only about ±50° C. This problem becomes even more serious as the use of In-free substrate holders becomes more widespread because the thermocouple is no longer in contact with the wafer. Infrared pyrometry is useful only above about 450° C. The pyrometer must be constantly recalibrated since the view port may become coated. This recalibration procedure can itself become a source of error. It is also important to pick a pyrometer with a narrow, short wavelength spectral window so that the temperature measured is that of the wafer and not that of the heater filaments behind it.

Substrate temperatures at only a single point can be evaluated by using reflection electron diffraction to observe the transition temperature at which <100>-GaAs surface reconstruction switches from As stabilized to Ga stabilized. This is taken as a measure of the bulk congruent sublimation temperature of GaAs, reported to be between 625° C. and 638° C.

Photoreflectance overcomes all of these problems since it directly measures the optical spectrum of the wafer to within several thousand angstroms from the surface. Also, it can readily be performed over a wide temperature range including T<450° C. It is relatively immune to viewport coating since it is a normalized technique. In addition, the quality and composition of epilayers such as $Ga_{1-x}Al_xAs$ can be determined during actual growth procedures.

The use of photoreflectance for the monitoring of MOCVD is particularly important. Since MOCVD is not an ultra-high vacuum (UHV) technique, many of the in-situ characterization tools available for MBE (which is UHV) such as RHEED, Auger, etc. cannot be used in MOCVD. In fact, optical means such as photoreflectance are the only way to gain in-situ information about the properties of the materials grown by MOCVD. These optical methods can be used under a variety of pressure conditions.

Such experiments depend crucially on the computer-controlled normalization and subtraction routine discussed above as well as on the ability to smooth and fit the lineshape in order to extract accurate values of the energy gaps. Because the materials can be measured up to 600° C., a lot of black-body radiation reaches the detector which must be subtracted from the true photoreflectance signal.

B. Electric Field Distributions At Semiconductor Heterostructive Interfaces

Photoreflectance can also be used as a contactless method to study electric field distributions and trap times at semiconductor heterostructure interfaces. The technique can be applied even when the heterostructures are fabricated on insulating substrates where it is not possible to use conventional methods such as capacitance-voltage and deeplevel transient spectroscopy measurements. The electric field distributions and trap times can be related to charges at the interfaces. The knowledge of the properties of these charges is very important for device applications.

Use is thereby made not only of the sharp, derivative-like features of photoreflectance but two new important aspects are also employed, i.e., the use of different pump wavelengths ($\lambda_p$) and modulating frequency ($\Omega_m$) dependence of the in-phase component of the photoreflectance signal. This permits investigation, for example, of the photoreflectance spectra at 300K from an MBE grown $Ga_{0.83}Al_{0.17}As/GaAs/GaAs$ (epilayer/buffer/substrate) heterostructure as a function of $\lambda_p$ (8200A°–4200A°) and $\Omega_m$ (20 Hz–4000 Hz). The buffer is semi-insulating GaAs. The sharp spectral features permit to observe the direct band gaps of the different parts of the structure, i.e., epilayer, buffer, substrate.

By using different $\lambda_p$, carriers can be photo excited in different regions of the structure and hence these separate sections can be selectively modulated.

By measuring the dependence of the in-phase component of the photoreflectance signal as a function of $\Omega_m$ it is possible to determine trap times at the various interfaces. The in-phase aspect is of importance for the following reason. Heretofore trap times were deduced from the dependence of the magnitude of the photoreflectance signal on $\Omega_m$. The magnitude of the signal is the sum of the squares of the in-phase and out-phase signals. However, this quantity does not obey the principle of superposition if there are contributions from traps of different time constants. Thus, it is rigorously correct for only a single trap state. For a multiple trap state it is necessary to evaluate the $\Omega_m$ dependence of the in-phase component (with respect to the pump beam) in order to employ the superposition of different trap time contributions.

The computer control of the pump-chopping frequency $\Omega_m$ as well as the accumulation of the in-phase (as well as out-phase) component of the signal is highly important for the success of such an experiment.

C. Determination of Strain at the $SiO_2/Si$ Interface

Photoreflectance can also be used to determine the strain in the Si at the $SiO_2/Si$ interface in structures prepared by thermal oxidation of Si and subjected to rapid thermal annealing.

Although GaAs and related materials such as GaAlAs are becoming more important, the workhorse of the electronics industry is still Si. One of the main reasons why electronic devices are fabricated from Si is because it is relatively easy to form a stable, insulating layer on the Si, i.e., $SiO_2$ on Si. Thus, the properties of the $SiO_2/Si$ interface are of considerable importance from a practical point of view.

The band gaps of semiconductors are functions of various externally applied parameters such as temperature, stress, etc. Thus, by evaluating the shifts of the energy gaps of semiconductors with one of these parameters, it is possible to gain information about the parameter.

In the $SiO_2/Si$ system, the photoreflectance spectrum from Si with no $SiO_2$ is determined (reference sample) and is then compared with the photoreflectance spectrum of $SiO_2/Si$ prepared and processed by different means. By comparing the shift of the photoreflectance peak of the Si in the $SiO_2/Si$ configuration with that of the reference Si, it is possible to deduce the stress that has been introduced by the formation of the $SiO_2$. Some of this stress can then be relieved by rapid thermal annealing. This is a very important aspect of making an actual Si device.

COMMERCIAL APPLICATIONS

The present invention is also of significance to commercial applications as contrasted to its use as a tool in research and development.

The future of electronic, photonic and optoelectronic devices depends on the manufacture of these complex devices by thin film techniques such as MBE and MOCVD as well as on various processing procedures. These systems are relatively complex and expensive. Thus yield is very important. There is a great need to characterize the materials and structures of these devices as well as to characterize various processing steps to improve yield and performance.

As discussed above, photoreflectance can yield a great deal of information about these systems. The apparatus in accordance with the present invention is relatively simple (and hence inexpensive), compact, easy to use and can readily be employed at room temperature. Photoreflectance gives more information per dollar of investment than almost any other characterization method. Many other characterization methods must be performed at cryogenic temperatures. In addition, since photoreflectance is contactless, it can be used before the samples are removed from the MBE or MOCVD growth chamber or processing chamber. This greatly reduces turn-around time for the operator of such a complex system to make adjustments.

Also, since photoreflectance is contactless and can be performed at 600° C. while the materials are actually being grown, it can be used to monitor and control growth parameters. This is of particular importance in MOCVD.

The following table is a summary of the present capabilities of the photoreflectance apparatus in accordance with the present invention.

Presently Known Capabilities of Photoreflectance Spectroscopy

I. Thin Film and Bulk Material

A. III-V and II-VI Binary Materials (GaAs, InP, CdTe)

1. Crystal Quality: Qualitative determination of crystal quality from lineshape of direct band gap ($E_o$) as well as higher lying transitions ($E_1, E_2$). One can also evaluate the effects of processinduced damage as well as annealing (laser, rapid thermal, etc.).
2. Carrier Concentration: In high quality material with a carrier concentration of about $10^{15}$-$10^{17}$ cm$^{-3}$ (n-type or p-type) it is possible to observe Franz-Kaldysh oscillations. The period of these oscillations yields the surface electric field and hence carrier concentration.
3. Passivation of Surface States: If the Franz-Kaldysh oscillations are observed then the effects of passivation of the surface and subsequent reduction of surface electric field can be studied.
4. Topographical Variations in Carrier Concentration but not Absolute Concentration- In the event that Franz-Kaldysh oscillations are not observed, it is still possible to get information in the low-field regime. In this region, the magnitude of the signal is proportional to net carrier concentration. Thus variation can be observed by measuring change in amplitude. This has been clearly demonstrated for contact electroreflectance but has yet to be shown for photoreflectance. It should work but has to be conclusively demonstrated.
5. Lattice-Mismatched Strains-Can evaluate lattice mismatched strains such as GaAs/Si, ZnSe/GaAs, etc.
6. Deep Trap States - From the dependence of the photoreflectance signal on the modulation frequency and temperature one can obtain trap activation energies. Already some important preliminary results have been obtained but more systems need to be studied. It requires a range of temperatures up to 200°-300° C.

B. Alloy Semiconductor

1. Quantitive determination of stoichiometry of alloy materials such as GaAlAs, GaInAs, AlInAs, GaAlSb, HgCdTe, etc. For HgCdTe, it requires 77K.
2. Crystal—Quality as explained above.
3. Deep Trap States—as explained above.

II. Heterostructures, Including Superlattices, Quantum Wells and Multiple Quantum Wells A. GaAs/GaAlAs System 1. Fundamental quantum transition corresponding to lasing frequency.
2. Higher-lying quantum transitions to evaluate parameters such as well and barrier widths, barrier heights, etc. Yields complete characterization of structure.
3. Two-Dimensional Electron Gas: One can observe signature of 2D-EG.

B. In GaAs/GaAs

1. Built-in strains.
2. Fundamental quantum transition, as explained above.
3. Characterization, as explained above.

C. GaSb/GaAlSb

1. Built-in strains
2. Fundamental quantum transitions, as explained above.
3. Characterization, as explained above.

While we have shown and described only one embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. A method of determining information in a semiconductor system about properties between two materials of different characteristics and different structural properties at an $SiO_2/Si$ interface of a semiconductor material involving an $SiO_2/Si$ system, comprising the steps of
   a) directing a probe beam of monochromatic light onto a material sample whose characteristics are to be determined,
   b) contactlessly electromodulating the sample by directing onto the same a modulated pump beam from a pump source to thereby modulate the built-in electric field at the surface/interface of the semiconductor system,
   c) collecting the light reflected from or transmitted by the sample with a detector which produces a d.c. signal and an a.c. signal which contains (i) a spurious signal caused by diffuse reflected light from the pump source and/or photoluminescence produced by the pump light reaching the detector and (ii) the true signal,
   d) normalizing the procedure to subtract the spurious signal from the true signal, and
   e) evaluating the shifts of energy gaps in the band gaps of the photoreflectance spectrum of the semiconductor material to obtain information about at least one externally applied parameter causing such shift.

2. A method according to claim 1, wherein one of the parameters is stress at the interface.

3. A method according to claim 1, wherein a photoreflectance spectrum of an Si reference sample having an Si peak and without $SiO_2$ is compared with a photoreflectance spectrum of $SiO_2$/Si prepared and processed by different means and having an Si peak, and wherein the stress introduced by the formation of $SiO_2$ is deduced by comparing the shift of the photoreflectance peak of the Si in the $SiO_2$/Si configuration with that of the Si reference sample.

4. A method of determining information in a semiconductor system about properties between two materials of different characteristics and different structural properties at an interface of a semiconductor material underneath an overlayer, comprising the steps of
   a) directing a probe beam of monochromatic light onto a material sample whose characteristics are to be determined,
   b) contactlessly electromodulating the sample by directing onto the same a modulated pump beam from a pump source to thereby modulate the built-in electric field at the surface/interface of the semiconductor system,
   c) collecting the light reflected from or transmitted by the sample with a detector which produces a d.c. signal and an a.c. signal which contains (i) a spurious signal caused by diffuse reflected light from the pump light reaching the detector and (ii) the true signal,
   d) normalizing the procedure to subtract the spurious signal from the true signal, and
   e) evaluating the shifts of energy gaps in the band gaps of the photoreflectance spectrum of the semiconductor material to obtain information about at least one externally applied parameter causing such shift, wherein a photoreflectance spectrum of a reference sample having a peak is compared with a photoreflectance spectrum of a semiconductor material system involving an interface and having a peak, and wherein the stress introduced at the interface is deduced by comparing the shift of the photoreflectance peak of the reference sample with that of the system involving an interface.

* * * * *